United States Patent [19]

Suarato et al.

[11] Patent Number: 5,744,454
[45] Date of Patent: Apr. 28, 1998

[54] ANTHRACYCLINE DERIVATIVES

[75] Inventors: Antonino Suarato; Michele Caruso; Alberto Bargiotti, all of Milan; Dario Ballinari, Milanese; Jacqueline Lansen, San Vittore Olona, all of Italy

[73] Assignee: Pharmacia & Upjohn S.p.A., Milan, Italy

[21] Appl. No.: 635,957

[22] PCT Filed: Sep. 5, 1995

[86] PCT No.: PCT/EP95/03480
§ 371 Date: May 6, 1996
§ 102(e) Date: May 6, 1996

[87] PCT Pub. No.: WO96/07665
PCT Pub. Date: Mar. 14, 1996

[30] Foreign Application Priority Data

Sep. 8, 1994 [GB] United Kingdom ............... 9148260

[51] Int. Cl.⁶ .............. A61K 31/70; C07H 15/24

[52] U.S. Cl. .................................... 514/34; 536/6.4
[58] Field of Search ............................ 536/6.4; 514/34

[56] References Cited

U.S. PATENT DOCUMENTS 5,637,572  6/1997  Merlini et al. ................... 514/34

OTHER PUBLICATIONS

Y. Levy, et al., *Traitement de L'amylose Al. sans myélome* Ann. Med. Interne, vol. 139 –1988 No. 3.

*Primary Examiner*—Elli Peselev
*Attorney, Agent, or Firm*—Oblon, Spivak, McClelland, Maier & Neustadt, P. C.

[57] ABSTRACT

The present invention provides the new use in the manufacture of a medicament for use in the treatment of amyloidosis of an anthracycline of formula A: wherein R1, R2, R3 and X are appropriate substituents. Novel compounds of the formula A, processes for their production and pharmaceutical compositions containing them are also described.

31 Claims, No Drawings

ANTHRACYCLINE DERIVATIVES

The present invention relates to treating amyloidosis, to novel compounds for such treatment, to processes for their preparation and to pharmaceutical compositions containing them.

The relationship between amyloidosis, cell death and loss of tissue function appears to be of relevance for different types of disorders including neurodegenerative disorders. Therefore, the prevention of amyloid formation and/or the induction of amyloid degradation can be an important therapeutic tool for all pathological disorders associated with amyloidosis including AL amyloidosis and neurodegenerative disorders of the Alzheimer's type.

More particularly, the present invention provides the use in the manufacture of a medicament for use in the treatment of amyloidosis of an anthracycline of formula A

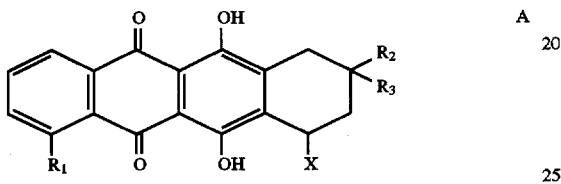

wherein $R_1$ represents:
  hydrogen or hydroxy;
  a group of formula $OR_4$ in which $R_4$ is $C_1$–$C_6$ alkyl, $C_5$–$C_6$ cycloalkyl or $CH_2Ph$, with the phenyl (Ph) ring optionally substituted by 1, 2 or 3 substituents selected from F, Cl, Br, $C_1$–$C_6$ alkyl, $C_1$–$C_6$ alkoxy and $CF_3$; or
  a group of formula $OSO_2R_5$ in which $R_5$ is $C_1$–$C_6$ alkyl or Ph optionally substituted by 1, 2 or 3 substituents selected from halogen such as F, Cl or Br, and $C_1$–$C_6$ alkyl;

$R_2$ represents hydrogen, hydroxy or $OR_4$ wherein $R_4$ is as above defined;

$R_3$ represents hydrogen, methyl or a group of formula $YCH_2R_6$ in which Y is CO, $CH_2$, CHOH or a group of formula

in which m is 2 or 3 and $R_6$ is:
  hydrogen or hydroxy;
  a group of formula $NR_7R_8$ in which:
    $R_7$ and $R_8$ are each independently selected from:
    a) hydrogen,
    b) a $C_1$–$C_6$ alkyl or $C_2$–C6 alkenyl group optionally substituted with hydroxy, CN, $COR_9$, $COOR_9$, $CONR_9R_{10}$, $O(CH_2)_nNR_9R_{10}$ (n is 2 to 4) or $NR_9R_{10}$, in which $R_9$ and $R_{10}$ are each independently selected from hydrogen, $C_1$–$C_{12}$ alkyl, $C_2$–$C_{12}$ alkenyl or phenyl optionally substituted by one or more, for example 1, 2 or 3, substituents selected from $C_1$–$C_6$ alkyl, $C_1$–$C_6$ alkoxy, F, Br, Cl, $CF_3$, OH, $NH_2$ or CN,
    c) $C_3$–$C_6$ cycloalkyl optionally substituted with $COR_9$, $COOR_9$ or OH, wherein $R_9$ is as above defined,
    d) phenyl $C_1$–$C_4$ alkyl or phenyl $C_2$–$C_4$ alkenyl optionally substituted on the phenyl ring by one or more, for example 1, 2 or 3, substituents selected from $C_1$–$C_6$ alkyl, $C_1$–$C_6$ alkoxy, F, Br, Cl, $CF_3$, OH, $NH_2$ or CN, and
    e) $COR_9$, $COOR_9$, $CONR_9R_{10}$, $COCH_2NR_9R_{10}$, $CONR_9COOR_{10}$ or $SO_2R_9$ in which $R_9$ and $R_{10}$ are as defined above, or or $R_7$ and $R_8$ together with nitrogen form:
  f) a morpholino ring optionally substituted with $C_1$–$C_4$ alkyl or $C_1$–$C_4$ alkoxy,
  g) a piperazino ring optionally substituted by $C_1$–$C_6$ alkyl, $C_2$–$C_6$ alkenyl or phenyl optionally substituted by one or more, for example 1, 2 or 3, substituents selected from $C_1$–$C_6$ alkyl, $C_1$–$C_6$ alkoxy, F, Br, Cl, $CF_3$, OH, $NH_2$ or CN, and
  h) a pyrrolidino, piperidino or tetrahydropyridino ring optionally substituted by OH, $NH_2$, COOH, $COOR_9$ or $CONR_9R_{10}$ wherein $R_9$ and $R_{10}$ are as above defined, $C_1$–$C_6$ alkyl, $C_2$–$C_6$ alkenyl or phenyl optionally substituted by one or more, for example 1, 2 or 3, substituents selected from $C_1$–$C_6$ alkyl, $C_1$–$C_6$ alkoxy, F, Br, Cl, $CF_3$, OH, $NH_2$, or CN;

a group of formula $OR_4$ or $SR_4$ in which $R_4$ is as above defined;

a group of formula O—Ph, wherein the phenyl (Ph) ring is optionally substituted by nitro, amino or $NR_7R_8$ as above defined; or a group of formula B or C:

wherein D is a group of formula $COOR_9$ or $CONR_7R_8$ in which $R_7$, $R_8$ and $R_9$ are as above defined; and X represents a sugar residue of formula X1 or X2

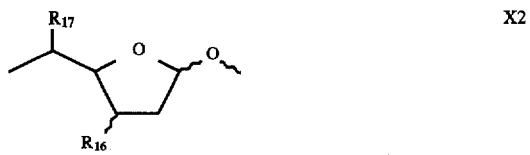

wherein:

$R_{11}$ and $R_{12}$ are both hydrogen or one of $R_{11}$ and $R_{12}$ is hydrogen and the other is F, Cl, Br or I;

$R_{13}$ represents hydrogen, hydroxy, $C_1$–$C_4$ alkoxy, amino, $NHCOCF_3$, $N=C(C_6H_5)_2$, $NHCOR_9$, $NHCONR_7R_8$ or a group of formula E or F

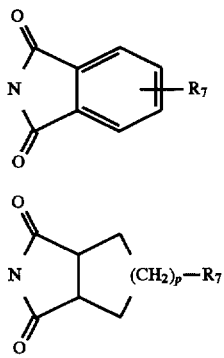

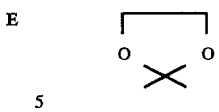

in which $R_7$, $R_8$ and $R_9$ are as above defined and p is 0 or 1;

$R_{14}$ and $R_{15}$ represent hydrogen, or one of $R_{14}$ and $R_{15}$ is hydrogen and the other is OH, F, Cl, Br, I or a group of formula $OSO_2R_5$ wherein $R_5$ is as above defined;

$R_{16}$ represents $CH_2OH$ or $R_{13}$ as above defined;

$R_{17}$ represents F, Cl, Br, I or a group of formula $OSO_2R_5$ wherein $R_5$ is as above defined;

and the pharmaceutically acceptable salts thereof; with the proviso that the compound of the formula A is not 4'-iodo-4'-deoxy-doxorubicin ($R_1$=$OCH_3$, $R_2$=OH, $R_3$=$COCH_2OH$, X=$X_1$, $R_{11}$=$R_{12}$=$R_{15}$=H, $R_{13}$=$NH_2$ and $R_{14}$=I).

In a further aspect of the present invention there are provided novel anthracyclines of the formula A as above defined, wherein:

X1 does not represent a residue in which both $R_{14}$ and $R_{15}$ are hydrogen atoms or one of $R_{14}$ or $R_{15}$ is hydroxy and $R_{13}$ is amino when $R_3$ is a group of formula $YCH_3$, $COCH_2NR_7'R_8'$, $COCH_2R'_4$ or $YCH_2OH$, wherein Y is as above defined, $R'_4$ is phenyl, benzyl, $C_1$-$C_6$ alkyl or $C_5$-$C_6$ cycloalkyl; $R'_7R'_8$ are each independently hydrogen, $C_1$-$C_{12}$ alkanoyl or, taken together, form a morpholino, piperazino or piperidino residue;

X1 does not represent a residue in which $R_{11}$ and $R_{12}$ are both hydrogen atoms, $R_{13}$ is amino and $R_{14}$ is iodine when $R_1$ is methoxy, $R_2$ is hydroxy and $R_3$ represents $COCH_2OH$. Each alkyl, alkoxy, or alkenyl group may be a straight chain or branched chain group.

A $C_1$-$C_{12}$ alkyl group is preferably a $C_1$-$C_6$ alkyl group. A $C_1$-$C_6$ alkyl group is preferably a $C_1$-$C_4$ alkyl group. A $C_1$-$C_6$ alkyl group is preferably methyl, ethyl, n-propyl, isopropyl, n-butyl, t-butyl, sec-butyl or n-pentyl. A $C_1$-$C_4$ alkyl group is preferably methyl, ethyl, n-propyl, isopropyl, n-butyl, t-butyl or sec-butyl.

A $C_3$-$C_6$ cycloalkyl group is preferably a $C_5$-$C_6$ cycloalkyl group. A $C_5$-C6 cycloalkyl group is preferably cyclopentyl or cyclohexyl.

A peptidyl residue may comprise up to 6, for example 1 to 4, amino acid residues. Suitable residues are Gly, Ala, Phe, Leu, Gly-Phe, Leu-Gly, Val-Ala, Phe-Ala, Leu-Phe, Phe-Leu-Gly, Phe-Phe-Leu, Leu-Leu-Gly, Phe-Tyr-Ala, Phe-Gly-Phe, Phe-Leu-Gly-Phe, Gly-Phe-Leu-Gly, Gly-Phe-Leu-Gly.

In the present invention $R_1$ is preferably hydrogen or methoxy. $R_2$ is preferably hydroxy. $R_3$ is preferably a group of formula $YCH_2R_6$ in which Y is CO or a group of formula:

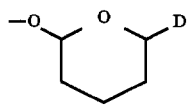

and $R_6$ is:
hydrogen or hydroxy;
a group of formula $NR_7R_8$ in which:
$R_7$ and $R_8$ are independently selected from:
a') hydrogen,
b') $C_1$-$C_4$ alkyl,
c') phenyl $C_1$-$C_2$ alkyl optionally substituted on the phenyl ring by one or two methoxy groups, and
d') $COCH_2NR_9R_{10}$ in which $R_9$ and $R_{10}$ are methyl groups,
or $R_7$ and $R_8$ together form:
e') a morpholino ring, or
f') a piperazino ring;
g') a tetrahydropyridino ring;
a group of formula O—Ph in which the phenyl (Ph) ring is optionally substituted by $NR_7R_8$ as above defined; or a group of formula

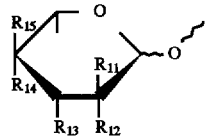

wherein D is a group of formula $CONR_7R_8$ wherein $NR_7R_8$ is as above defined; and X represents a sugar residue of formula X1

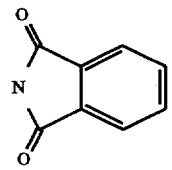

wherein:

$R_{11}$ and $R_{12}$ represent hydrogen of one of $R_{11}$ or $R_{12}$ is hydrogen and the other is I;

$R_{13}$ represents amino, $NHCOCF_3$, $N=C(C_6H_5)_2$ or a group of formula $R_{14}$ and $R_{15}$ represent hydrogen or one or $R_{14}$ or $R_{15}$ is hydrogen and the other is OH, I or $OSO_2CH_3$.

The present invention provides the salts of those compounds of formula A that have salt-forming groups, especially the salts of the compounds having a carboxylic group, a basic group (e.g. an amino group).

The salts are especially physiologically tolerable salts, for example alkali metal and alkaline earth metal salt (e.g. sodium, potassium, lithium, calcium and magnesium salts), ammonium salts, salts with an appropriate organic amine or amino acid (e.g. arginine, procaine salts) and the addition salts formed with suitable organic or inorganic acids, for example hydrochloric acid, sulfuric acid, carboxylic acid and sulfonic organic acids (e.g. acetic, trifluoroacetic, p-toluensulphonic acid).

The present invention encompasses all the possible stereoisomers as well as their racemic or optically active mixtures.

Specific examples of the preferred compounds of the present invention are those listed hereinunder:

A1: 14-N-(morpholino)-3'-N-trifluoroacetyl-4'iododaunomycin

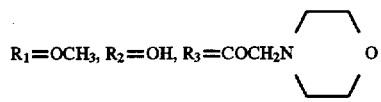

$R_{11}=R_{12}=R_{15}=H, R_{13}=NHCOCF_3, R_{14}=I$

A2: 14-N-(3,4-dimethoxybenzylamino)-3'-N-trifluoroacetyl-4'-iodo-daunomycin $R_1=OCH_3$, $R_2=OH$, $R_3=COCH_2NHCH_2[C_6H_3(OCH_3)_2]$, $R_{11}=R_{12}=R_{15}=H, R_{13}=NHCOCF_3, R_{14}=I$ A3: 14-O-[2-(1-piperazinyl)-carbonyltetrahydropyran-6yl]-3'-N-trifluoroacetyl-4'-iododaunomycin $R_1=OCH_3, R_2=OH,$

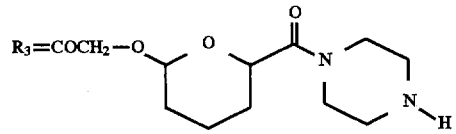

$R_{11}=R_{12}=R_{15}=H, R_{13}=NHCOCF_3, R_{14}=I$

A4: 14-[p-(dimethylaminocarbonylamino)-phenyloxy]-3'-N-trifluoroacetyl-4'- iododaunomycin $R_1=OCH_3$, $R_2=OH$, $R_3=COCH_2O-C_6H_4[pNHCOCH_2N(CH_3)_2]$, $R_{11}=R_{12}=R_{15}=H, R_{13}=NHCOCF_3, R_{14}=I$ A5: 13-deoxo-13-ethylenedioxy-14-N-(morpholino)-3'-N-trifluoro-acetyl-4'-iododaunomycin trifluoro-acetyl-4'-iododaunomycin

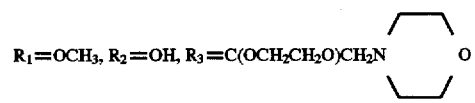

$R_{11}=R_{12}=R_{15}=H, R_{13}=NHCOCF_3, R_{14}=I$

A6: 13-deoxo-13-ethylenedioxy-14-[p-dimethylaminocarbonyl-amino)phenyloxy]-3'-N-trifluoroacetyl-4'-iododaunomycin $R_1=OCH_3$, $R_2=OH$, $R_3=C(OCH_2CH_2O)CH_2O$ [pNHCOCH_2N(CH_3)_2], $R_{11}=R_{12}=R_{15}=H, R_{13}=NHCOCF_3, R_{14}=I$ A7: 13-dihydro-14-N-(morpholino)-3'-N-trifluoroacetyl-4'-iodo-daunomycin

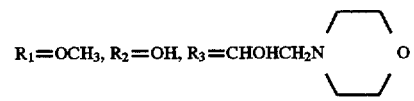

$R_{11}=R_{12}=R_{15}=H, R_{13}=NHCOCF_3, R_{14}=I$

A8: 14-N-(morpholino)-3'-N-phthaloyl-4'-iododaunomycin

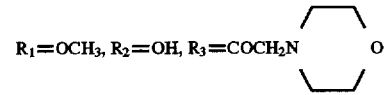

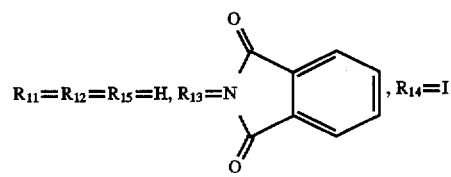

A9: 14-N-(3,4-dimethoxybenzylamino)-3'-N-phthaloyl-4'iododaunomycin $R_1=OCH_3, R_2=OH, R_3=COCH_2NHCH_2[C_6H_5(OCH_3)_2]$

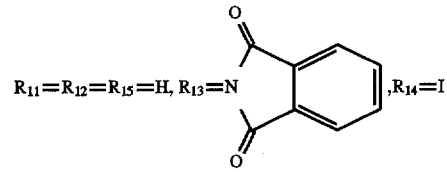

A10: 14-O-[2-(1-piperazinyl)-carbonyltetrahydropyran-6-yl]-3'-N-phthaloyl-4'-iododaunomycin $R_1=OCH_3, R_2=OH,$

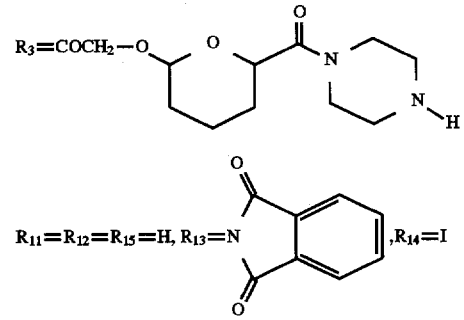

A11: 14-N-(morpholino)-3'-N-trifluoroacetyl-4'-methanesulfonate-daunomycin

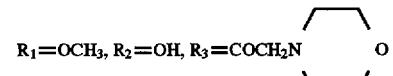

$R_{11}=R_{12}=R_{15}=H, R_{13}=NHCOCF_3, R_{14}=OSO_2CH_3$

A12: 14-O-[2-(1-piperazinyl)-carbonyltetrahydropyran-6-yl]-3'-N-trifluoroacetyl-4'-methanesulfonatedaunomycin $R_1=OCH_3, R_2=OH,$

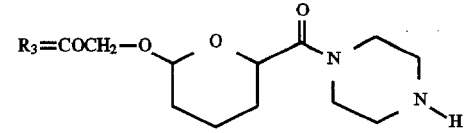

$R_{11}=R_{12}=R_{15}=H, R_{13}=NHCOCF_3, R_{14}=OSO_2CH_3$

A13: 14-[p-(dimethylaminocarbonylamino)phenyloxy]-3'-N-trifluoroacetyl-4'-methanesulfonatedaunomycin $R_1=OCH_3$, $R_2=OH$, $R_3=COCH_2O-C_6H_4$ [pNHCOCH_2N(CH_3)_2], $R_{11}=R_{12}=R_{15}=H$, $R_{13}=NHCOCF_3, R_{14}=OSO_2CH_3$ A14: 14-N-(morpholino)-3'-N-phthaloyl-4'-methanesulfonatedaunomycin

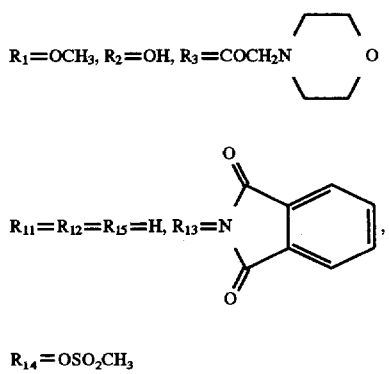

$R_1=OCH_3, R_2=OH, R_3=COCH_3, R_{11}=R_{12}=R_{15}=H,$
$R_{12}=NC(C_6H_5)_2, R_{15}=OH$ $R_{14}=OSO_2CH_3$

A15: 3'-N-diphenylmethylene-4'-epidaunorubicin
$R_1=OCH_3, R_2=OH, R_3=COCH_3, R_{11}=R_{12}=R_{14}=H,$
$R_{12}=NC(C_6H_5)_2, R_{15}=OH$ A16: 3'-N-diphenylmethylene-4'-iododoxorubicin
$R_1=OCH_3$, $R_2=OH$, $R_3=COCH_2OH$,
$R_{11}=R_{12}=R_{15}=H, R_{12}=NC(C_6H_5)_2, R_{14}=I$ A17: 14-N-(morpholino)-3'-N-diphenylmethylene-4'-iododaunomycin

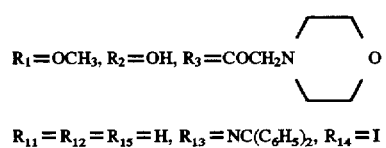

$R_1=OCH_3, R_2=OH, R_3=COCH_2N\frown O$ $R_{11} = R_{12} = R_{15} = H, R_{13} = NC(C_6H_5)_2, R_{14} = I$ A18: 4-demethoxy-2'-iodo-daunorubicin $R_1=H, R_2=OH,$
$R_3=COCH_3$, $R_{11}=R_{15}=H$, $R_{12}=I$, $R_{13}=NH_2$,
$R_{14}=OH$ The compounds of formula A may be prepared, depending on the nature of the substituents, starting from known anthracyclines by appropriate chemical modifications of the aglycone or the sugar moiety or both part of the molecule, or by coupling anthracyclinones with sugars.

Processes for preparing compounds of formula A and pharmaceutically acceptable salts thereof are as follows:

(i) A preferred process for the preparation of compounds of formula A wherein $R_3$ is a group of formula $COCH_2NR_7R_8$, wherein $R_7$ and $R_8$ are as above defined with the proviso that $R_7$ and $R_8$ do not represent the groups $COR_9$, $CONR_9R_{10}$, $CONR_9COOR_{10}$ or $SO_2R_9$ in which $R_9$ and $R_{10}$ are as above defined, comprises:

1) converting a compound of formula G

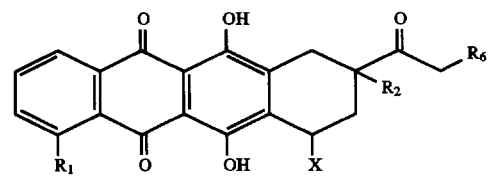

wherein $R_6$ is hydrogen, $R_1$, $R_2$ and X are as above defined, with the proviso that no alkenyl residues are present in G and, in the sugar residue X, $R_{13}$ does not represent hydroxy when one of the other substituents of X is hydroxy, into the corresponding 14-bromo derivative, then (2) reacting the resulting bromo derivative of formula H

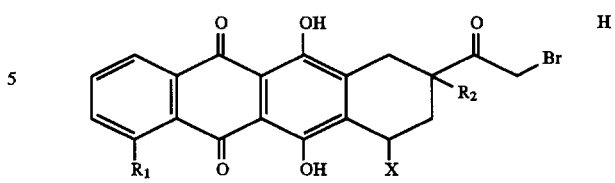

wherein $R_1$, $R_2$ and X are as above defined, with the appropriate amine of formula $NHR_7R_8$, wherein $R_7$ and $R_8$ are as above defined with the proviso that $R_7$ and $R_8$ do not represent the groups $COR_9$, $CONR_9R_{10}$, $CONR_9COOR_{10}$ or $SO_2R_9$ as above defined, and, if desired, converting the resulting said compound of formula A into a pharmaceutically acceptable salt thereof.

(ii) In another example, compounds of formula A, defined as under (i) above may be further transformed into other anthracyclines of formula A in which one or both of $R_7$ and $R_8$ represents a group of formula $COR_9$ or $SO_2R_9$ wherein $R_9$ is as above defined, by reacting a 14-amino derivative of formula A as defined under (i), with the proviso that one or both of $R_7$ and $R_8$ represents a hydrogen atom, with an acyl derivative of formula $HalCOR_9$ or $HalSO_2R_9$, wherein Hal is halogen and $R_9$ is as above defined, and, if desired, converting the resulting said compound of formula A into a pharmaceutically acceptable salt thereof.

(iii) In another example, a preferred process for the preparation of compounds of formula A wherein $R_3$ is a group of formula B or C as above defined, with the proviso that $R_1$ and substituents of the sugar residue X do not represent primary hydroxy groups comprises:

(1) reacting a compound represented by the formula G in which $R_6$ is hydroxy, and $R_1$ and X are as above defined, with a compound of formula B1 or C1

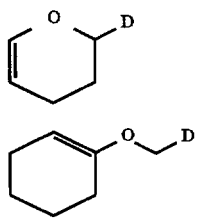

wherein D is as above defined and, if desired, deblocking the masked hydroxy groups, and, if desired, converting the resulting said compound of formula A into a pharmaceutically acceptable salt thereof.

In another example, a preferred process for the preparation of compounds of formula A wherein $R_3$ is $CHOHCH_2R_6$, comprises reducing a compound of formula A in which $R_3$ represents $COCH_2R_6$, wherein $R_6$ is as above defined with the proviso that no additional ketone groups are present in A, and, if desired, converting the resulting said compound of formula A into a pharmaceutically acceptable salt thereof.

(v) In another example, a preferred process for the preparation of compounds of formula A wherein $R_3$ is a group of formula $CH_2CH_2R_6$, comprises:

(1) transforming a compound of formula A in which $R_3$ is $COCH_2R_6$, with the proviso that no additional ketone groups are present in A, into a 13-(substituted)-benzensulfonylhydrazone, preferably 13-(p-fluoro)-benzensulfonylhydrazone, then (2) reducing it in conditions capable of preserving the glycosidic bond, and, if desired, converting the resulting said compound of formula A into a pharmaceutically acceptable salt thereof.

(vi) In another example, a process for the preparation of compounds of formula A wherein $R_{11}$ and $R_{12}$ are both hydrogen atoms, comprises:

(1) condensing an aglycone of formula K

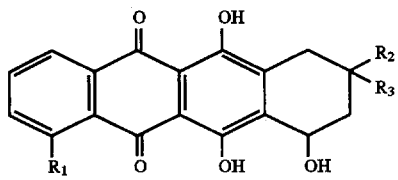

K wherein $R_1$, $R_2$ and $R_3$ are as above defined, with the proviso that $R_1$, $R_2$ and $R_3$ do not represent groups bearing free primary or secondary hydroxy groups, with a sugar derivative of formula L1 or L2

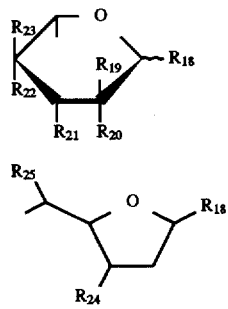

L1

L2 wherein $R_{18}$ represents a suitable leaving group such as a halogen atom, for example a chlorine atom, or an activated ester residue, such as $OCOCF_3$ or $OCO(pNO_2C_6H_5)$, $R_{19}$ and $R_{20}$ are hydrogen atoms, $R_{21}$ is hydrogen, $C_{1-C_4}$ alkoxy, an ester residue such as $OCOCF_3$ or $OCO(pNO_2C_6H_5)$ or the group $NHCOCF_3$, $R_{22}$ and $R_{23}$ are both hydrogen or one of $R_{22}$ or $R_{23}$ is hydrogen and the other is an ester residue such as $OCOCF_3$ or $OCO(pNO_2C_6H_5)$ or the group $NHCOCF_3$, $R_{24}$ is $CH_2OCOCF_3$ or has the same meaning as $R_{21}$ above defined and $R_{25}$ represents $OCOCF_3$ or $OCO(pNO_2C_6H_5)$, then (vi) deblocking the amino and hydroxy groups, and, if desired, converting the resulting said compound of formula A into a pharmaceutically acceptable thereof.

(vii) In another example, a preferred process for the preparation of compounds of formula A wherein $R_{13}$ is E or F comprises:

(1) reacting an anthracycline of formula A as above defined, which has only a primary amino group, with a halo-acyl derivative of formula E1 or F1

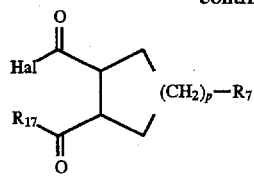

E1

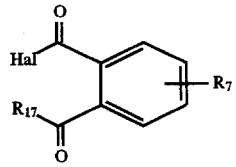

F1 wherein $R_7$ is as above defined, Hal represents halogen atom and $R_{17}$ is an alkoxy residue, preferable ethoxy, and, if desired, (2) treating the resultant mono-amino-acyl derivative with base to form groups of formula E or F and, if desired, converting the resulting said compound of formula A into a pharmaceutically acceptable salt thereof.

The compounds of formula A as defined under (i) may be prepared as described in DE-A-2,557,537, for example by reacting a compound of formula H as above defined, prepared from compound G according to the disclosure of DE-A-1,197,874 with from 1 to 1.2 equivalents of the appropriate amine of formula $NHR_7R_8$, wherein $R_7$ and $R_8$ are as above defined with the proviso that $R_7$ and $R_8$ do not represent a group of formula $COR_9$, $CONR_9R_{10}$, $CONR_9COOR_{10}$ or $SO_2R_9$ as above defined, in a dry polar solvent such as acetone or dimethyl-formamide, at a temperature of about 0° to 30° C., preferably at room temperature, for from 4 to 24 hours, and, if desired, converting the resulting said compound of formula A into a pharmaceutically acceptable salt thereof, preferably with anhydrous hydrogen chloride in methanol.

The compounds of formula A as defined under (ii) may be prepared by reacting a compound of formula A, defined as under (i), with an acyl derivative of formula $HalCOR_9$ or $HalSO_2R_9$, wherein Hal is halogen and $R_9$ is as above defined, in dry polar solvent such as acetone or dimethylformamide, at a temperature of about 0° to 30° C., preferably at room temperature, for from 4 to 24 hours.

The compounds of formula A as defined under (iii) may be prepared as described in WO 92/10212 and WO 92/02255, for example by reacting an anthracycline as defined under (iii)(1) with derivatives of formula B1 or C1 in an aprotic solvent such as methylene chloride in the presence of an acid catalyst, such as pyridinium p-toluenesulfonate, at a temperature of from 10° to 30° C., preferably at room temperature, and from 3 to 24 hours, and, if desired, converting the resulting said compound of formula A into a pharmaceutically acceptable salt thereof, preferably with anhydrous hydrogen chloride in methanol; or by hydrolyzing the ester derivative with dilute aqueous sodium hydroxide.

The compounds of formula A as defined under (iv) may be prepared by reducing anthracyclines of formula A, as defined under (iv), in water or in one or more organic solvents, depending on the nature of the compound, or by means of microbial reduction. For example, water soluble anthracyclines are reduced in water at a pH from 8 to 9, preferably pH 8.5, in the presence of a reducing agent such as sodium borohydride, at a temperature of from 0° C. to room temperature and for from 1 to 10 minutes as described in Gaz. Chim. Ital., 114,185 (1984). Water insoluble anthracyclines are preferably dissolved in an anhydrous aprotic organic solvent, such as dry tetrahydrofuran, cooled to −50°C., treated with 1.5 equivalents of magnesium bromide etherate and 1.5 equivalents of sodium borohydride for from 5 to 30 minutes, then added dropwise with methanol. The 13-dihydro derivative of formula A, as above defined, is recovered from the reaction mixture by extracting with methylene chloride and washing with water. Microbial reduction of anthracyclines as defined under (iv) may be performed, for example, by using a blocked mutant of *Streptomyces peucetius* as described in Gaz. Chim. Ital., 114, 185 (1984).

The compounds of formula A as defined under (v) may be prepared as described in GB-A-2238540, for example by reducing the 13-[(4-fluoro)benzenesulfonyl]hydrazone derivative of an anthracycline of formula A, as defined under (v)(1), with sodium cyanoborohydride in an organic solvent, such as toluene or dimethylformamide, at a temperature of from 25° to 80° C., for from 6 to 24 hours.

The compounds of formula A, as defined under (vi), may be prepared by condensing an anthracyclinone of formula K, as above defined, by a Koening-Knorr reaction with a halosugar derivative of formula L1 or L2 as above defined, in a dry apolar solvent, such as dry methylene chloride, in the presence of a condensing agent such as mercuric oxide, mercuric bromide, and molecular sieves as described in DE-A-2,525,633. An alternative procedure comprises condensing an anthracyclinone of formula K with a halosugar derivative of formula L1 or L2 as above defined, in a dry apolar solvent, such as dry methylene chloride, with silver trifluoromethanesulfonate dissolved in ethyl ether, at temperature of from 0° to 25° C., for from 1 to 6 hours, as described in BE-A-842,930.

The compounds of formula A as defined under (vii) may be prepared by reacting an anthracycline, which has only a primary amino group, with a halo derivative of formula E1 or F1 as above defined, in an organic solvent such as tetrahydrofuran or dimethylformamide, at from 0° C. to room temperature, for from 1 to 24 hours. The mono-acyl derivative is further treated with a condensing agent such as tetrabutyl ammonium fluoride to afford the cyclic acyl anthracycline.

Other anthracyclines of formula A may be analogously prepared starting from known compounds by means of known procedures.

For example, the following compounds are known and can be represented by the same formula A in which X represents a sugar of formula X1:

daunorubicin (A19: $R_1$=OCH$_3$, $R_2$=OH, $R_3$=COCH$_3$, $R_{11}$=$R_{12}$=$R_{15}$=H, $R_{13}$=NH$_2$, $R_{14}$=OH), doxorubicin (A20: $R_1$=OCH$_3$, $R_2$=OH, $R_3$=COCH$_2$OH, $R_{11}$=$R_{12}$=$R_{15}$=H, $R_{13}$=NH$_2$, $R_{14}$=OH), 4-demethoxydaunorubicin (A21: $R_1$=H, $R_2$=OH, $R_3$=COCH$_3$, $R_{11}$=$R_{12}$=$R_{15}$=H, $R_{13}$=$_{NH2}$, $R_{14}$=OH), 4demethoxydoxorubicin (A22: $R_1$=H, $R_2$=OH, $R_3$=COCH$_2$OH, $R_{11}$=$R_{12}$=$R_{15}$=H, $R_{13}$=NH$_2$, $R_{14}$=OH), 4'-epidaunorubicin (A23: $R_1$=OCH$_3$, $R_2$=OH, $R_3$=COCH$_3$, $R_{11}$=$R_{12}$=$R_{14}$=H, $R_{13}$=NH$_2$, $R_{15}$=OH),4'-epidoxorubicin (A24: $R_1$=OCH$_3$, $R_2$=OH, $R_3$=COCH$_2$OH, $R_{11}$=$R_{12}$=$R_{14}$=H, $R_{13}$=NH$_2$, $R_{15}$=OH), 4'-deoxydaunorubicin (A25: $R_1$=OCH$_3$, $R_2$=OH, $R_3$=COCH$_3$, $R_{11}$=$R_{12}$=$R_{14}$=$R_{15}$=H, $R_{13}$=NH$_2$), 4'-deoxydoxorubicin (A26: $R_1$=OCH$_3$, $R_2$=OH, $R_3$=COCH$_2$OH, $R_{11}$=$R_{12}$=$R_{14}$=$R_{15}$=H, $R_{13}$=NH$_2$), 4'-iododaunorubicin (A27: $R_1$=OCH$_3$, $R_2$=OH, $R_3$=COCH$_3$, $R_{11}$=$R_{12}$=$R_{15}$=H, $R_{13}$=NH$_2$, $R_{14}$=I), 4'-iododoxorubicin (A28: $R_1$=OCH$_3$, $R_2$=OH, $R_3$=COCH$_2$OH, $R_{11}$=$R_{12}$=$R_{15}$=H, $R_{13}$=NH$_2$, $R_{14}$=I), 9-deoxydauno-rubicin (A29: $R_1$=OCH$_3$, $R_2$=H, $R_3$=COCH$_3$, $R_{11}$=$R_{12}$=$R_{15}$=H, $R_{13}$=NH$_2$, $R_{14}$=OH), 9-deoxydoxorubicin (A30: $R_1$=OCH$_3$, $R_2$=H, $R_3$=COCH$_2$OH, $R_{11}$=$R_{12}$=$R_{15}$=H, $R_{13}$=NH$_2$, $R_{14}$=OH), 9-deacetyldaunorubicin (A31: $R_1$=OCH$_3$, $R_2$=OH, $R_3$=H, $R_{11}$=$R_{12}$=$R_{15}$=H, $R_{13}$=NH$_2$, $R_{14}$=OH), 9-deacetyl-9-deoxydaunorubicin (A32: $R_1$=OCH$_3$, $R_2$=$R_3$=H, $R_{11}$=$R_{12}$=$R_{15}$=H, $R_{13}$=NH$_2$, $R_{14}$=OH), 9-deacetyl-9-hydroxymethylendaunorubicin (A33: $R_1$=OCH$_3$, $R_2$=CH$_2$OH, $R_3$=H, $R_{11}$=$R_{12}$=$R_{15}$=H, $R_{13}$=NH$_2$, $R_{14}$=OH), 13-dihydro-daunorubicin (A34: $R_1$=OCH$_3$, $R_2$=OH, $R_3$=CHOHCH$_3$, $R_{11}$=$R_{12}$=$R_{15}$=H, $R_{13}$=NH$_2$, $R_{14}$=OH), 13-dihydrodoxorubicin (A35: $R_1$=OCH$_3$, $R_2$=OH, $R_3$=CHOHCH$_2$OH, $R_{11}$=$R_{12}$=$R_{15}$=H, $R_{13}$=NH$_2$, $R_{14}$=OH), 13-dihydro-4-demethoxydaunorubicin (A36: $R_1$=H, $R_2$=OH, $R_3$=CHOHCH$_3$, $R_{11}$=$R_{12}$=$R_{15}$=H, $R_{13}$=NH$_2$, $R_{14}$=OH), 13-dihydro-4'-epidaunorubicin (A37: $R_1$=OCH$_3$, $R_2$=OH, $R_3$=CHOHCH$_3$, $R_{11}$=$R_{12}$=$R_{14}$=H, $R_{13}$=NH$_2$, $R_{15}$=OH), 13-dihydro-4'-epidoxorubicin (A38: $R_1$=OCH$_3$, $R_2$=OH, $R_3$=CHOHCH$_2$OH, $R_{11}$=$R_{12}$=$R_{14}$=H, $R_{13}$=OH), 13-dihydro-4'iododoxorubicin (A39: $R_1$=OCH$_3$, $R_2$=OH, $R_3$=CHOHCH$_2$OH, $R_{11}$=$R_{12}$=$R_{15}$=H, $R_{13}$=NH$_2$, $R_{134}$=I), 13-deoxodaunorubicin (A40: $R_1$=OCH$_3$, $R_2$=OH, $R_3$=CH$_2$CH$_3$, $R_{11}$=$R_{12}$=$R_{15}$=H, $R_{13}$=NH$_2$, $R_{14}$=OH), N-trifluoroacetyl-daunorubicin (A41: $R_1$=OCH$_3$, $R_2$=OH, $R_3$=COCH$_3$, $R_{11}$=$R_{12}$=$R_{15}$=H, $R_{13}$=NHCOCF$_3$, $R_{14}$=OH), N-trifluoroacetyldoxorubicin (A42: $R_1$=OCH$_3$, $R_2$=OH, $R_3$=COCH$_2$OH, $R_{11}$=$R_{12}$=$R_{15}$=H, $R_{13}$=NHCOCF$_3$, $R_{14}$=OH), N-trifluoro-acetyl-4demethoxydaunorubicin (A43: $R_1$=H, $R_2$=OH, $R_3$=COCH$_3$, $R_{11}$=$R_{12}$=$R_{15}$=H, $R_{13}$=NHCOCF$_3$, $R_{14}$=OH) N-trifluoroacetyl-4'-epidauno-rubicin (A44: $R_1$=OCH$_3$, $R_2$=OH, $R_3$=COCH$_3$, $R_{11}$=$R_{12}$=$R_{14}$=H, $R_{13}$=NHCOCF$_3$, $R_{15}$=OH), N-trifluoroacetyl-4'-iododaunorubicin (A45: $R_1$=OCH$_3$, $R_2$=OH, $R_3$=COCH$_3$, $R_{11}$=$R_{12}$=$R_{15}$=H, $R_{13}$=$_{NHCOCF3}$, $R_{14}$=I) (see: F. Arcamone in "Doxorubicin" Medicinal Chemistry, vol.17, Academic Press 1981) or 4'-deoxy-4'-methanesulfonate-daunorubicin (A46: $R_1$=OCH$_3$, $R_2$=OH, $R_3$=COCH$_3$, $R_{11}$=$R_{12}$=$R_{15}$=H, $R_{13}$=NH$_2$, $R_{14}$=OSO$_2$CH$_3$), 4'-deoxy-4'-methanesulfonate-doxorubicin (A47: $R_1$=OCH$_3$, $R_2$=OH, $R_3$=COCH$_2$OH, $R_{11}$=$R_{12}$=$R_{15}$=H, $R_{13}$=NH$_2$, $R_{14}$=OSO$_2$CH$_3$) (see WO 95/16693). Some of the above mentioned anthracyclines, in particular 4'-epidoxorubicin, are also preferred compounds within the scope of the present invention.

Also some aglycones, used for the preparation of anthracyclines of formula A as described under (vi), are known and can be represented by formula K as above defined, for example:

daunomycinone (K1: $R_1$=OCH$_3$, $R_2$=OH, $R_3$'COCH$_3$), adriamycinone (K2: $R_1$=OCH$_3$, $R_2$=OH, $R_3$=COCH$_2$OH), 4-demethoxydaunomycinone (K3: $R_1$=H, $R_3$=OH, $R_3$=COCH$_3$). Also some sugars, used for the preparation of anthracyclines of formula A as described under (vi) are known and can be represented by formula M:

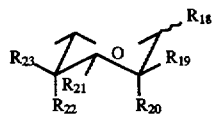

M such as the amino sugars daunosamine, 3-amino-2,3,6-trideoxy-L-lyxo-hexopyranose, (M1: $R_{18}$=OH, $R_{19}=R_{20}=R_{23}=H$, $R_{21}=NH_2$, $R_{22}=OH$) (see: J. Am. Chem. Soc., 86, 5334, 1964) or acosamine, 3-amino-2,3,6-tri-deoxy-L-arabino-hexopyranose, (M2: $R_{18}=OH$, $R_{19}=R_{20}=R_{22}=H$, $R_{21}=NH_2$, $R_{23}=OH$) (see: J. Med. Chem., 18, 703, 1975) or the corresponding 1-chloro-3,4-ditrifluoroacetyl daunosaminyl derivatives (M3: $R_{18}=Cl$, $R_{19}=R_{20}=R_{23}=H$, $R_{21}=NHCOCF_2$, $R_{22}=OCOCF_3$) or 1-chloro3,4-ditri-fluoroacetyl acosaminyl derivatives (M3: $R_{18}=Cl$, $R_{19}=R_{20}=R_{22}=H$, $R_{21}=NHCOCF_3$, $R_{23}=OCOCF_3$) or deamino-sugars such as L-fucose (M4: $R_{18}=R_{19}=R_{21}=R_{22}=OH$, $R_{20}=R_{23}=H$) and L-rhamnose (M5: $R_{18}=R_{20}=R_{21}=R_{23}=OH$, $R_{19}=R_{22}=H$).

The compounds of the present invention are characterized by high inhibitory activity on amyloidosis.

The term amyloidosis indicates various diseases whose common characteristic is the tendency of particular proteins to polymerize and precipitate, as insoluble fibrils, into the extracellular space causing structural and functional damage to organ and tissues. The classification of amyloid and amyloidosis has been recently revised in Bulletin of the World Health Organisation 71(1): 105 (1993).

All the different types of amyloid share the same ultra-structural organization in anti-parallel β-pleated sheets despite the fact that they contain a variety of widely differing protein subunits [see: Glenner G. G., New England J. Med. 302 (23): 1283 81980)]. AL amyloidosis is caused by peculiar monoclonal immunoglobulin light chains which form amyloid fibrils. These monoclonal light chains are produced by monoclonal plasma cells with a low mitotic index which accounts for their well known insensitivity to chemotherapy. The malignacy of these cells consists in their protidosynthetic activity.

The clinical course of the disease depends on the selectivity of organ involvement; the prognosis can be extremely unfavourable in case of heart infiltration (median survival <12 months) or more benign in case of kidney involvement (median survival approx. 5 years).

Considering the relative insensitivity of the amyloidogenic deposits to proteolytic digestion, a molecule that can block or slow amyloid formation and increase the solubility of existing amyloid deposits seems the only reasonable hope for patients with AL amyloidosis. Furthermore, since the supermolecular organization of the amyloid fibrilis is the same for all types of amyloid, the availability of a drug that interferes with amyloid formation and increase the solubility of existing deposits, allowing clearance by normal mechanisms, could be of great benefit for all types of amyloidosis, and in particular for the treatment of Alzheimer's disease.

Indeed, the major pathological feature of Alzheimer's Disease (AD), Down's Syndrome, Dementia pugilistica and Cerebral amyloid angiopaty is amyloid deposition in cerebral parenchyma and vessel walls. These markers are associated with neuronal cell loss in cerebral cortex, limbic regions and subcortical nuclei. Several studies have shown that selective damage to various neuronal systems and synapse loss in the frontal cortex has been correlated with cognitive decline. The pathogenesis and molecular basis of neurodegenerative processes in AD is not known, but the role of β-amyloid, deposited in brain parenchyma and vessel walls has been highlighted by recent report of its neurotoxic activity in vitro and in vivo (Yanker et al. Science, 245: 417, 1990. Kowall et al. PNAS, 88: 7247, 1991). Furthermore, the segregation of familiar AD with mutation of the amyloid precursor protein (APP) gene has aroused interest in the potential pathogenetic function of β-amyloid in AD [Mullan M. et al. TINS, 16(10): 392 (1993)].

The neurotoxicity of β-amyloid has been associated with the fibrillogenic properties of protein. Studies with homologous synthetic peptides indicate that hippocampal cells were insensitive to exposure to fresh β1-42 solution for 24 h while their viability decreased when neurons were exposed to β1-42 previously stored in saline solution for 2–4 days at 37° C. to favour the peptide aggregation. The relationship between fibrils and neurotoxicity is further supported by recent evidence showing that the soluble form of β-amyloid is produced in vivo and in vitro during normal cellular metabolism (Hass et al. Nature, 359, 322, 1993) and only when it aggregate in congophilic formation was associated with distrophic nevrites. On the other hand, non-congophilic "preamyloid" formation containing single molecule of β-amyloid was not associated with neuronal alteration (Tagliavini et al. Neurosci. Lett. 93: 191, 1988).

The neurotoxicity of β-amyloid has also been confirmed using a peptide homologue β-amyloid fragment 25-35(β25-35) reteining the self-aggregating properties of the complete β-amyloid fragment β142.

Chronic but not acute exposure of hippocampal neurons to micromolar concentration of β25-35 induced neuronal death by the activation of a mechanism of programmed cell death known as apoptosis (Forloni et al. NeuroReport, 4: 523, 1993). Here again, neurotoxicity was associated with the self aggregating propertiy of β25-35.

Other neurodegenerative disorders such as spongiform encephalopathy (SE) are characterized by neuronal death and extracellular deposition of amyloid, in this case originated from Prion (PrP) protein. In analogy with the observation that β-amyloid is neurotoxic, the effects of synthetic peptides homologous to different segments of PrP on the viability of primary rat hippocampal neurons have been investigated. The chronic application of peptide corresponding to PrP 106–126 induced neuronal death by apoptosis while under the same conditions all the other peptides tested and the scrambled sequence of PrP 106–126 did not reduce cell viability (Forloni et al., Nature 362: 543). PrP 106–126 resulted highly fibrilogenic in vitro and when stained with Congo red, the peptide aggregate showed green biifrangence indicative of the β-sheets conformation characteristic of amyloid.

The compounds of the present invention can be used to make medicaments useful to prevent or arrest the progression of diseases caused by amyloid proteins, such as AL amyloidosis, Alzheimer or Down's Syndrome and the like.

The present invention also includes, within its scope, pharmaceutical compositions comprising one or more compounds of formula A, or pharmaceutically acceptable salts thereof, as active ingredients, in association with pharmaceutically acceptable carriers, excipients or other additives, if necessary.

The pharmaceutical compositions containing a compound of formula A or salts thereof may be prepared in a conventional way by employing conventional non-toxic pharmaceutical carriers or diluents in a variety of dosage forms and ways of administration.

In particular, the compounds of the formula A can be administered:

A) orally, for example, as tablets, troches, lozenges, aqueous or oily suspension, dispersible powders or granules, emulsions, hard or soft capsules, or syrups or elixirs. Compositions intended for oral use may be prepared according to any method known in the art for the manufacture of pharmaceutical compositions and such compositions may contain one or more agents selected from the group consisting of sweetening agents, flavouring agents, coloring agents and preserving agents in order to provide pharmaceutically elegant and palatable preparations.

Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, maize starch or alginic acid; binding agents, for example maize starch, gelatin or acacia, and lubrificating agents, for example magnesium stearate or stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. Formulation for oral use may also be presented as hard gelatin capsules wherein the active ingredient is mixed with an inert solid diluent, for example, calcium carbonate, calcium phosphate or kaolin, or a soft gelatin capsules wherein the active ingredient is mixed with water or an oil medium, for example, peanut oil, liquid paraffin or olive oil. Aqueous suspensions contain the active materials in admixture with excipients suitable for the manufacture of aqueous suspensions.

Such excipients are suspending agents, for example, sodium carboxymethylcellulose, methylcellulose, hydroxypropylmethyl cellulose, sodium alginate, polyvinylpyrrolidone gum tragacanth and gum acacia; dispersing or wetting agents may be naturally-occurring phosphatides, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and a hexitol anhydrides, for example polyoxyethylene sorbitan monooleate. The said aqueous suspensions may also contain one or more preservatives, for example, ethyl or n-propyl p-hydroxybenzoate, one or more coloring agents, one or more flavouring agents, or one or more sweetening agents, such as sucrose or saccharin. Oily suspension may be formulated by suspending the active ingredient in a vegetable oil, for example arachis oil, olive oil, seseme oil or coconut oil or in a mineral oil such as liquid paraffin. The oily suspensions may contain a thickening agent, for example beewax, hard paraffin or cetyl alcohol. Sweetening agents, such as those set forth above, and flavouring agents may be added to provide a palatable oral preparation. These compositions may be preserved by the addition of an autoxidant such as ascorbic acid. Dispersible powders and granules suitable for preparation of an aqueous suspension by the addition of water provide the active ingredient in admixture with a dispersing or wetting agent, a suspending agent and one or more preservatives. Suitable dispersing or wetting agents and suspending agents are exemplified by those already mentioned above. Additional excipients, for example sweetening, flavouring and agents, may also be present.

The pharmaceutical compositions of the invention may also be in the form of oil-in-water emulsions. The oily phase may be a vegetable oil, for example olive oil or arachis oils, or a mineral oil for example liquid paraffin or mixtures of these.

Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan mono-oleate, and condensation products of the said partial esters with ethylene oxide, for example polyoxy ethylene sorbitan monooleate. The emulsion may also contain sweetening and flavouring agents. Syrups and elixirs may be formulated with sweetening agents, for example glycerol, sorbitol or sucrose. Such formulations may also contain a demulcent, a preservative and flavouring and coloring agents.

B) Parenterally, either subcutaneously or intravenously or intramuscularly, or intrasternally, or by infusion techniques, in the form of sterile injectable aqueous or olagenous suspension. The pharmaceutical compositions may be in the form of a sterile injectable aqueous or olagenous suspensions.

These suspensions may be formulated according to the known art using those suitable dispersing of wetting agents and suspending agents which have been above. The sterile injectable preparation may also be a sterile injectable solution or suspension in a non-toxic parenterally-acceptable diluent or solvent for example, as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium.

For this purpose any bland fixed oils may be conventionally employed including synthetic mono- or diglycerides. In addition fatty acids such as oleic acid find use in the preparation of injectables;

Still a further object of the present invention is to provide a method of controlling amyloidosis diseases by administering a therapeutically effective amount of one or more of the active compounds encompassed by the formula A in humans in need of such treatment.

Daily doses are in the range of about 0.1 to about 50 mg per kg of body weight, according to the activity of the specific compound, the age, weight and conditions of the subject to be treated, the type and the severity of the disease, and the frequency and route of administration; preferably, daily dosage levels are in the range of 5 mg to 2 g. The amount of active ingredient that may be combined with the carrier materials to produce a single dosage form will vary depending upon the host treated and the particular mode of administration. For example, a formulation intended for oral intake may contain from 5 mg to 2 g of active agent compounded with an appropriate and convenient amount of carrier material which may vary from about 5 to about 95 percent of the total composition. Dosage unit forms will generally contain between from about 5 mg to about 500 mg of the active ingredient.

The following Examples illustrate the invention without limiting it.

EXAMPLE 1

Preparation of 14-N-(morpholino)-3'-N-trifluoroacetyl-4'-iododaunomycin (A1)

4'-iododaunorubicin hydrochloride (A27, 1.34 g, 2 mmol) was dissolved in a mixture of dioxane (30 ml) and methanol (20 ml) and treated with a solution of 10% bromine in chloroform (2 ml) at 0° C. as described in U.S. Pat. No. 4,438,105. After 1 hour the reaction mixture was added with ethyl ether (200 ml) and the precipitate was collected, washed with ethyl ether (100 ml), redissolved with anhydrous tetrahydrofuran (80 ml) and treated with morpholine (0.25 ml), overnight at room temperature. After that, the reaction mixture was concentrated to small volume under reduced pressure, diluted with methylene chloride, cooled at 0° C. and treated with a solution of trifluoroacetic anhydride (2 ml) in methylene chloride (10 ml). After 30 minutes the reaction mixture was washed with aqueous 5% sodium hydrogen carbonate and twice with water. The organic phase was concentrated under reduced pressure and flash chromatographed on silica gel using a mixture of methylene chloride/methanol (90:10 v/v) as eluting system to afford the title compound A1 that was converted in the corresponding hydrochloride by addition of the stoichiometric amount of hydrogen chloride, followed by precipitation with ethyl ether. Yield: 0.9 g.

TLC on Kieselgel $F_{254}$ (Merck), eluting system methylene chloride/methanol (90:10 v/v) $R_1$=0.5

FD-MS: m/e 816 $[M]^+$

EXAMPLE 2

Preparation of 13-dihydro-14-N-(morpholino)-3'-N-trifluoroacetyl-4'-iododaunomycin (A7)

14-N-(morpholino)-3'-N-trifluoroacetyl-4'-iododaunomycin (A1, 0.4 g, 0.05 mmol), prepared as described in Example 1, in the form of free base, was dissolved with anhydrous tetrahydrofuran (20 ml) and added with magnesium bromide etherate (0.7 g). After 10 minutes at room temperature, under nitrogen, the mixture was cooled at −50° C., added with sodium borohydride (50 mg) then treated with anhydrous methanol (2×2 ml) in 5 minutes. After that, acetone (5 ml) was added. The reaction mixture was brought to 0° C. and extracted with 0.1 aqueous hydrochloric acid. The water phase was brought to pH 8.5 with 0.1 sodium hydroxide and extracted with methylene chloride to give the title compound A2 that was converted in the corresponding hydrochloride by addition of the stoichiometric amount of hydrogen chloride, followed by precipitation with ethyl ether.

Yield: 0.3 g.

TLC on Kieselgel $F_{254}$ (Merck), eluting system methylene chloride and methanol (90:10 v/v) $R_1$=0.3

FD-MS: m/e 818 $[M]^+$

EXAMPLE 3

Preparation of 14-N-(3,4-dimethoxybenzylamino)-3'-N-trifluoroacetyl-4'-iododaunomycin (A2)

The title compound A2 was prepared by reacting 14-bromo-4'-iododaunomycin (0.65g, 1 mmol) with 3,4dimethoxybenzylamine (0.3 g, 2mmol) in anhydrous tetrahydrofurane (50ml) as described in Example 1. Yield 0.3g. TLC on Kieselgel $F_{254}$ (Merck) eluting system methylene chloride/methanol (90:10 v/v) $R_1$=0.45.

FD-MS: m/e 797 $[M]^+$

EXAMPLE 4

Preparation of 14-N-(morpholino)-3'-N-phthaloyl-4'-iododaunomycin (A8)

14-N-(morpholino)-4'-iododaunomycin (0.7g, 1 mmol) prepared as described in Example 1, was reacted with phthaloyl chloride (0.4g, 2mmol) in anhydrous tetrahydrofurane (50ml) at 0° C. for 4 hours. The mixture was diluted with methylene chloride (100 ml) and washed with aqueous sodium hydrogen carbonate and water, then was dried over anhydrous sodium sulphate. The solvent was removed under reduced pressure and the crude material was flash chromatographed on silica gel using a mixture of methylene chloride and acetone (95:5 v/v) as eluting system to give the title compound A8 (0.5g). TLC on Kieselgel $F_{254}$ (Merck) eluting system methylene chloride/methanol (90:10 v/v) $R_f$0.25.

FD-MS: m/e 851 $[M]^+$

EXAMPLE 5

Preparation of 3'-N-diphenylmethylene-4'-iododoxorubicin (A16)

Iododoxorubicin hydrochloride (A27, 0.65g, 1 mmol) was dissolved in tetrahydrofurane (50ml) and treated with benzophenone imine (0.36g, 2mmol). The mixture was kept at room temperature overnight, then the solvent was removed under reduced pressure and the crude material was flash chromatographed on silica gel to give the title compound A16 (0.6g). TLC on Kieselgel $F_{254}$ (Merck) eluting system methylene chloride/acetone (95:5 v/v) $R_f$0.55

FD-MD: m/e 816 $[M]^+$

EXAMPLE 6

Preparation of 14-N-(morpholino)-3'-N-diphenylmethylene-4'-iododaunorubicin (A17)

14-N-(morpholino)-4'-iododaunomycin (0.7g, 1 mmol), prepared as described in Example 1, was reacted with with benzophenone imine (0.36g, 2mmol) as described in Example 5 to give the title compound A17 (0.65g). TLC on Kieselgel $F_{254}$ (Merck) eluting system methylene chloride/acetone (95:5 v/v) $R_1$=0.40.

FD-MS: m/e 885 $[M]^+$

Biological test.

Anthracycline derivatives of formula A interfere with the self-aggregating activity of β-amyloid fragment 25–35 and PrP fragment 106–126 by using light scattering analysis.

β25–35 (GSNKGAIIGLH) and PrP 106–126 (KTNMKHMAGAAAAGAVVGGLG) were synthesized using solid phase chemistry by a 430A Applied Biosystems Instruments and purified by reverse-phase HPLC (Beckman Inst. mod 243) according to Forloni et al., Nature 362: 543, 1993.

Light scattering of the peptide solutions was evaluated by spectrofluorimetry (Perkin Elmer LS 50B), excitation and emission were monitored at 600 nm. β-amyloid fragment 25–35 and PrP 106–126 were dissolved at a concentration of 0.5 to 1 mg/ml (0.4–0.8 mM and 0.2–0.4 mM respectively) in a solution of phosphate buffer pH 5, 10 mM spontaneously aggregate within an hour.

13-Dihydro-4'-iododoxorubicin (A39), dissolved at several concentration (0.2–2 mM) in Tris buffer 5 mM pH 7.4, was added to the peptidic solutions at the moment of their preparation in order to evaluate the process of fibrilogenesis.

Compound A39, added at equimolar concentration with β-amyloid fragment 25–35 and PrP 106–126, showed complete prevention of the aggregation.

We claim:

1. A method of treating amyloidosis comprising administering to a patient in need thereof an effective amount of an anthracycline of formula

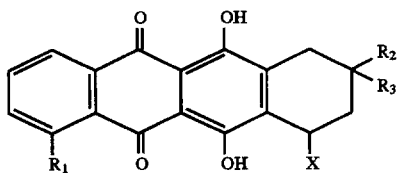

Wherein $R_1$ represents:
hydrogen or hydroxy;
a group of formula $OR_4$ in which $R_4$ is $C_1$–$C_6$ alkyl, $C_5$–$C_6$ cycloalkyl or $CH_2Ph$, with the phenyl(Ph) ring optionally substituted by 1, 2 or 3 substituents selected from the group consisting of F, Cl, Br, $C_1$–$C_6$ alkyl, $C_1$–$C_6$ alkoxy and $CF_3$; or
a group of formula $OSO_2R_5$ in which $R_5$ is $C_1$–$C_6$ alkyl or Ph optionally substituted by 1, 2 or 3 substituents selected from the group consisting of halogen such as F, Cl or Br and $C_1$–$C_6$ alkyl;

$R_2$ represents hydrogen, hydroxy or $OR_4$ as above defined;

$R_3$ represents hydrogen, methyl or a group of formula $YCH_2R_6$ in which Y is CO, $CH_2$, CHOH or a group of formula

in which m is 2 or 3 and
$R_6$ is hydrogen or hydroxy;
a group of formula $NR_7R_8$ in which
$R_7$ and $R_8$ are each independently selected from the group consisting of:
a) hydrogen,
b) a $C_1$–$C_6$ alkyl or $C_2$–$C_6$ alkenyl group optionally substituted with hydroxy, CN, $COR_9$, $COOR_9$, $CONR_9R_{10}$, $O(CH_2)_nNR_9R_{10}$ (n is 2 to 4) or $NR_9R_{10}$, in which $R_9$ and $R_{10}$ are each independently selected from the group consisting of hydrogen, $C_1$–$C_{12}$ alkyl, $C_2$–$C_{12}$ alkenyl or phenyl optionally substituted by one or more substituents selected from the group consisting of $C_1$–$C_6$ alkyl, $C_1$–$C_6$ alkoxy, F, Br, Cl, $CF_3$, OH, $NR_2$ or CN,
c) $C_3$–$C_6$ cycloalkyl optionally substituted with $COR_9$, $COOR_9$ or OH, wherein $R_9$ is as above defined,
d) phenyl $C_1$–$C_4$ alkyl or phenyl $C_2$–$C_4$ alkenyl optionally substituted on the phenyl ring by one or more, substituents selected from the group consisting of $C_1$–$C_6$ alkyl, $C_1$–$C_6$ alkoxy, F, Br, Cl, $CF_3$, OH, $NH_2$ or CN,
e) $COR_9$, $COOR_9$, $CONR_9R_{10}$, $COCH_2NR_9R_{10}CONR_9COOR_{10}$, $SO_2R_9$ in which $R_9$ and $R_{10}$ are as above defined, or
$R_7$ and $R_8$ together with nitrogen form:
f) a morpholino ring optionally substituted with $C_1$–$C_4$ alkyl or $C_1$–$C_4$ alkoxy,
g) a piperazino ring optionally substituted by $C_1$–$C_6$ alkyl, $C_2$–$C_6$ alkenyl or phenyl optionally substituted by one or more, substituents selected from the group consisting of $C_1$–$C_6$ alkyl, $C_1$–$C_6$ alkoxy, F, Br, Cl, $CF_3$, OH, $NH_2$ or CN, and
h) a pyrrolidino or piperidino or tetrahydropyridino ring optionally substituted by OH, $NH_2$, COOH, $COOR_9$ or $CONR_9R_{10}$ wherein $R_9$ and $R_{10}$ are as above defined, $C_1$–$C_6$ alkyl, $C_2$–$C_6$ alkenyl or phenyl optionally substituted by one or more substituents selected from the group consisting of $C_1$–$C_6$ alkyl, $C_1$–$C_6$ alkoxy, F, Br, Cl, $CF_3$, OH, $NH_2$, or CN;
a group of formula $OR_4$ or $SR_4$ in which $R_4$ is as above defined;
a group of formula O—Ph, wherein the phenyl (Ph) ring is optionally substituted by nitro, amino or $NR_7R_8$ as above defined; or
a group of formula B or C:

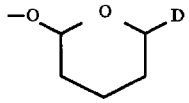

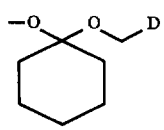

wherein D is a group of formula $COOR_9$ or $CONR_7R_8$ in which $R_7$, $R_8$ and $R_9$ are as above defined; and
X represents a sugar residue of formula X1 or X2

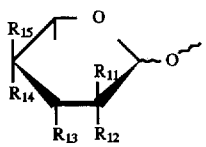

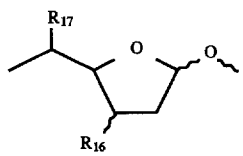

wherein:
$R_{11}$ and $R_{12}$ are both hydrogen or one of $R_{11}$ and $R_{12}$ is hydrogen and the other is F, Cl, Br or I;
$R_{13}$ represents hydrogen, hydroxy, $C_1$–$C_4$ alkoxy, amino, $NHCOCF_3$, $N=C(C_6H_5)_2$, $NHCOR_9$, $NHCONR_7R_8$ or a group of formula E or F

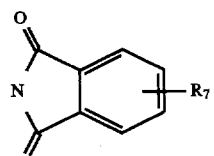

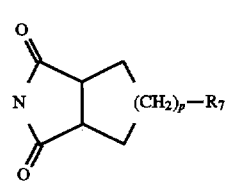

in which $R_7$, $R_8$ and $R_9$ are as above defined and p is 0 or 1;
$R_{14}$ and $R_{15}$ represent hydrogen or one of $R_{14}$ or $R_{15}$ is hydrogen and the other is OH, F, Cl, Br, I or a group of formula $OSO_2R_5$ wherein $R_5$ is as above defined;
$R_{16}$ represents $CH_2OH$ or $R_{13}$ as above defined;
$R_{17}$ represents F, Cl, Br, I or a group of formula $OSO_2R_5$ wherein $R_5$ is as above defined;

and pharmaceutically acceptable salts thereof; with the proviso that the compound of the formula A is not 4'-iodo-4'-deoxy-doxorubicin.

2. The method according to claim 1 wherein the amyloidosis is AL amyloidosis, Alzheimer's disease or Down's syndrome.

3. The method of claim 1, wherein said administering comprises administering a dosage unit form containing from 5 to 500 mg of the compound of formula A or pharmaceutically acceptable salt thereof.

4. The method of claim 1 wherein $R_3$ represents methyl or a group of formula $YCH_2R_6$ in which Y is CO, $CH_2$, CHOH or a group of formula

in which m is 2 or 3 and
$R_6$ is hydrogen or hydroxy.

5. An anthracycline of formula A

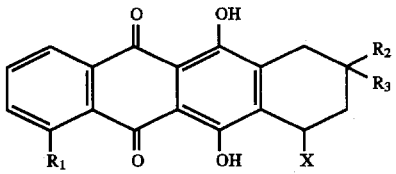

wherein $R_1$ represents:
hydrogen or hydroxy;
a group of formula $OR_4$ in which $R_4$ is $C_1$–$C_6$ alkyl, $C_5$–$C_6$ cycloalkyl or $CH_2Ph$, with the phenyl(Ph) ring optionally substituted by 1, 2 or 3 substituents selected from the group consisting of F, Cl, Br, $C_1$–$C_6$ alkyl, $C_1$–$C_6$ alkoxy and $CF_3$; and
a group of formula $OSO_2R_5$ in which $R_5$ is $C_1$–$C_6$ alkyl or Ph optionally substituted by 1, 2 or 3 substituents selected from the group consisting of halogen such as F, Cl or Br and $C_1$–$C_6$ alkyl;
$R_2$ represents hydrogen, hydroxy or $OR_4$ as above defined;
$R_3$ represents methyl or a group of formula $YCH_2R_6$ in which Y is CO, $CH_2$, CHOH or a group of formula

in which m is 2 or 3 and
$R_6$ is hydrogen or hydroxy;
a group of formula $NR_7R_8$ in which
$R_7$ and $R_8$ are each independently selected from the group consisting of:
a) hydrogen,
b) a $C_1$–$C_6$ alkyl or $C_2$–$C_6$ alkenyl group optionally substituted with hydroxy, CN, $COR_9$, $COOR_9$, $CONR_9R_{10}$, $O(CH_2)_nNR_9R_{10}$ (n is 2 to 4) or $NR_9R_{10}$, in which $R_9$ and $R_{10}$ are each independently selected from hydrogen, $C_1$–$C_{12}$ alkyl, $C_2$–$C_{12}$ alkenyl or phenyl optionally substituted by one or more substituents selected from $C_1$–$C_6$ alkyl, $C_1$–$C_6$ alkoxy, F, Br, Cl, $CF_3$, OH, $NR_2$ or CN,
c) $C_3$–$C_6$ cycloalkyl optionally substituted with $COR_9$, $COOR_9$ or OH, wherein $R_9$ is as above defined, d) phenyl $C_1$–$C_4$ alkyl or phenyl $C_2$–$C_4$ alkenyl optionally substituted on the phenyl ring by one or more, substituents selected from the group consisting of $C_1$–$C_6$ alkyl, $C_1$–$C_6$ alkoxy, F, Br, Cl, $CF_3$, OH, $NH_2$ or CN,
e) $COR_9$, $COOR_9$, $CONR_9R_{10}$, $COCH_2NR_9R_{10}CONR_9COOR_{10}$, $SO_2R_9$ in which $R_9$ and $R_{10}$ are as above defined, or $R_7$ and $R_8$ together with nitrogen form:
f) a morpholino ring optionally substituted with $C_1$–$C_4$ alkyl or $C_1$–$C_4$ alkoxy,
g) a piperazino ring optionally substituted by $C_1$–$C_6$ alkyl, $C_2$–$C_6$ alkenyl or phenyl optionally substituted by one or more, substituents selected from the group consisting of $C_1$–$C_6$ alkyl, $C_1$–$C_6$ alkoxy, F, Br, Cl, $CF_3$, OH, $NH_2$ and CN, and
h) a pyrrolidino or piperidino or tetrahydropyridino ring optionally substituted by OH, $NH_2$, COOH, $COOR_9$ or $CONR_9R_{10}$ wherein $R_9$ and $R_{10}$ are as above defined, $C_1$–$C_6$ alkyl, $C_2$–$C_6$ alkenyl or phenyl optionally substituted by one or more substituents selected from the group consisting of $C_1$–$C_6$ alkyl, $C_1$–$C_6$ alkoxy, F, Br, Cl, $CF_3$, OH, $NH_2$, and CN;

a group of formula $OR_4$ or $SR_4$ in which $R_4$ is as above defined;
a group of formula O—Ph, wherein the phenyl (Ph) ring is optionally substituted by nitro, amino or $NR_7R_8$ as above defined; or
a group of formula B or C:

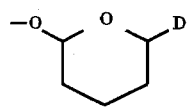

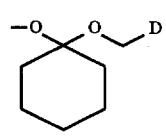

wherein D is a group of formula $COOR_9$ or $CONR_7R_8$ in which $R_7$, $R_8$ and $R_9$ are as above defined; and
X represents a sugar residue of formula X1 or X2

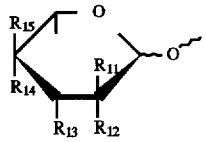

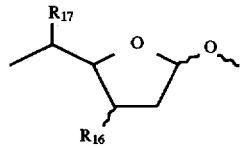

wherein:

$R_{11}$ and $R_{12}$ are both hydrogen or one of $R_{11}$ and $R_{12}$ is hydrogen and the other is F, Cl, Br or I;

$R_{13}$ represents hydrogen, hydroxy, $C_1$–$C_4$ alkoxy, amino, $NHCOCF_3$, $N=C(C_6H_5)_2$, $NHCOR_9$, $NHCONR_7R_8$ or a group of formula E or F

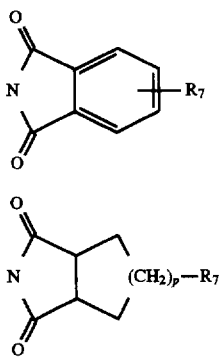

in which $R_7$, $R_8$ and $R_9$ are as above defined and p is 0 or 1;

$R_{14}$ and $R_{15}$ represent hydrogen or one of $R_{14}$ or $R_{15}$ is hydrogen and the other is OH, F, Cl, Br, I or a group of formula $OSO_2R_5$ wherein $R_5$ is as above defined;

$R_{16}$ represents $CH_2OH$ or $R_3$ as above defined;

$R_{17}$ represents F, Cl, Br, I or a group of formula $OSO_2R_5$ wherein $R_5$ is as above defined;

with the proviso:

that the compound of the formula A is not 4'-iodo-4'-deoxy-doxorubicin or

X1 does not represent a residue in which both $R_{14}$ and $R_{15}$ are hydrogen atoms or one or $R_{14}$ or $R_{15}$ is hydroxy, and $R_{13}$ is amino when $R_3$ is a group of formula $YCH_3$, $COCH_2NR'_7R'_8$, $COCH_2R'_4$ or $YCH_2OH$ wherein Y is defined in claim 1, $R'_4$ is phenyl, benzyl, $C_{1-6}$ alkyl or $C_{5-6}$ cycloalkyl, $R_7'$ and $R_8'$ are each independently hydrogen, $C_{1-12}$ alkanoyl or, taken together, form a morpholino, piperazino or piperidino residue or X1 does not represent a residue in which both $R_{11}$ and $R_{12}$ are hydrogen atoms, $R_{13}$ is amino and $R_{14}$ is iodine when $R_1$ is methoxy $R_1$ is hydroxy and $R_3$ represents $COCH_2OH$.

6. The anthracycline of claim 5, wherein said anthracycline is 14-N-(morpholino)-3'-N-trifluoroacetyl-4'-iododaunomycin.

7. The anthracycline of claim 5 wherein said anthracycline is 14-N-(3,4-dimethoxybenzylamino)-3'-N-trifluoroacetyl-4'-iodo-daunomycin.

8. The anthracycline of claim 5 wherein said anthracycline is 14-O-[2-(1-piperazinyl)carbonyltetrahydropyran-6-yl]-3'-N-trifluoroacetyl-4'-iododaunomycin.

9. The anthracycline of claim 5 wherein said anthracycline is 14-[p-(dimethylaminocarbonylamino)phenyloxy]-3'-N-trifluoroacetyl-4'-iododaunomycin.

10. The anthracycline of claim 5 wherein said anthracycline is 13-deoxo-13-ethylenedioxy-14-N-(morpholino)3'-N-trifluoro-acetyl-4'-iododaunomycin.

11. The anthracycline of claim 5 wherein said anthracycline is 13-deoxo-13-ethylenedioxy-14-[p-dimethylaminocarbonyl-amino)phenyloxy]-3'-N-trifluoroacetyl-4'-iododaunomycin.

12. The anthracycline of claim 5 wherein said anthracycline is 13-dihydro-14-N-(morpholino)-3'-N-trifluoroacetyl-4'-iodo-daunomycin.

13. The anthracycline of claim 5 wherein said anthracycline is 14-N-(morpholino)-3'-N-phthaloyl-4'-iododaunomycin.

14. The anthracycline of claim 5 wherein said anthracycline is 14-N-(3,4-dimethoxybenzylamino)-3'-N-phthaloyl-4'-iododaunomycin.

15. The anthracycline of claim 5 wherein said anthracycline is 14-O-[2-(1-piperazinyl)-carbonyltetrahydropyran-6-yl]-3'-N-phthaloyl-4'-iododaunomycin.

16. The anthracycline of claim 5 wherein said anthracycline is 14-N-(morpholino)-3'-N-trifluoroacetyl-4'-methanesulfonate-daunomycin.

17. The anthracycline of claim 5 wherein said anthracycline is 14-O-[2-(1-piperazinyl)-carbonyltetrahydropyran-6yl]3'-N-trifluoroacetyl-4'-methanesulfonatedaunomycin.

18. The anthracycline of claim 5 wherein said anthracycline is 14-[p-(dimethylaminocarbonylamino)phenyloxy]-3'-N-trifluoroacetyl-4'-methanesulfonatedaunomycin.

19. The anthracycline of claim 5 wherein said anthracycline is 14-N-(morpholino)-3'-N-phthaloyl-4'-methanesulfonate-daunomycin.

20. The anthracycline of claim 5 wherein said anthracycline is 3'-N-diphenylmethylene-4'-epidaunorubicin.

21. The anthracycline of claim 5 wherein said anthracycline is 3'-N-diphenylmethylene-4'-iododoxorubicin.

22. The anthracycline of claim 5 wherein said anthracycline is 14-N-(morpholino)-3'-N-diphenylmethylene-4'-iododaunomycin.

23. The anthracycline of claim 5 wherein said anthracycline is 4-demethoxy-2'-iodo-daunorubicin.

24. A process for producing an anthracycline of formula A as defined in claim 5 wherein $R_3$ is a group of formula $COCH_2NR_7R_{10}$, wherein $R_7$ and $R_8$ are as defined in claim 4 with the proviso that $R_7$ and $R_8$ do not represent the groups $COR_9$, $CONR_9R_{10}$, $CONR_9COOR_{10}$ or $SO_2R_9$ in which $R_9$ and $R_{10}$ are as defined in claim 5, which process comprises:

1) converting a compound of formula G

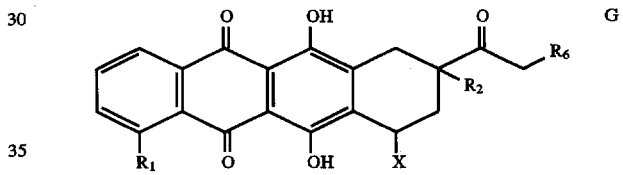

wherein $R_6$ is hydrogen, $R_1$, $R_2$ and X are as above defined, with the proviso that no alkenyl residues are present in G and, in the sugar residue X, $R_{13}$ does not represent hydroxy when one of the other substituents of X is hydroxy, into the corresponding 14-bromo derivative, then 2) reacting the resulting bromo derivative of formula H

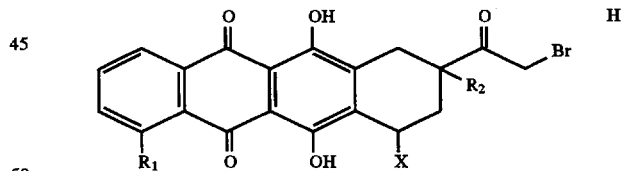

wherein $R_1$, $R_2$ and X are as above defined, with the appropriate amine of formula $NHR_7R_8$, wherein $R_7$ and $R_8$ are as above defined with the proviso that $R_7$ and $R_8$ do not represent the groups $COR_9$, $CONR_9R_{10}$ $CONR_9COOR_{10}$ or $SO_2R_9$ as above defined; and, if desired, converting the resulting said compound of formula A into a pharmaceutically acceptable salt thereof.

25. A process for producing an anthracycline of formula A as defined in claim 5 wherein one or both of $R_7$ and $R_8$ is a group of formula $COR_9$ or $SO_2R_9$ wherein $R_9$ is as defined in claim 5, by reacting a 9-amino derivative of formula A wherein $R_3$ is a group of formula $COCH_2NR_7R_8$, wherein $R_7$ and $R_8$ are as defined in claim 5 with the proviso that $R_7$ and $R_8$ do not represent the groups $COR_9$, $CONR_9R_{10}$, or $SO_2R_9$ in which $R_9$ and $R_{10}$ are as defined in claim 5 with the proviso that one or both of $R_7$ and $R_8$ represents hydrogen, with an acyl derivative of formula $HalCOR_9$ or $HalSO_2R_9$, wherein Hal is halogen and $R_9$ is as above defined in claim 5; and, if desired, converting the resulting said compound of formula A into a pharmaceutically acceptable salt thereof.

26. A process for producing an anthracycline of formula A as defined in claim 5 wherein $R_3$ is a group of formula B or C as defined in claim 5, with the proviso that the $R_1$ substituents of the sugar residue X do not represent primary hydroxy groups; which process comprises:

1) reacting a compound represented by the formula G in which $R_6$ is hydroxy, and $R_1$ and X are as defined in claim 4, with compound of formula B1 or C1 or C1

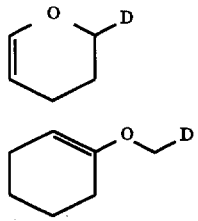

wherein D is as defined in claim 4 and, if desired, deblocking the masked hydroxy groups, and, if desired, converting the resulting said compound of formula A into a pharmaceutically acceptable salt thereof.

27. A process for producing an anthracycline of formula A as defined in claim 5 wherein $R_3$ is $CHOHCH_2R_6$, which comprises reducing a compound of formula A in which $R_3$ represents $COCH_2R_6$, wherein $R_6$ is as defined in claim 5, with the proviso that no additional ketone groups are present in A; and, if desired, converting the resulting said compound of formula A into a pharmaceutically acceptable salt thereof.

28. A process for producing an anthracycline of formula A as defined in claim 5 wherein $R_3$ is a group of formula $CH_2CH_2R_6$, which comprises:

(1) transforming a compound of formula A in which $R_3$ is $COCH_2R_6$, with the proviso that no additional ketone groups are present in A, into a 13-(substituted) benzensulfonylhydrazone, preferably 13-(p-fluoro) benzensulfonylhydrazone, then 2) reducing it in conditions capable of preserving the glycosidic bond; and, if desired, converting the resulting said compound of formula A into a pharmaceutically acceptable salt thereof.

29. A process for producing anthracycline of formula A as defined in claim 5 wherein $R_{11}$ and $R_{12}$ are both hydrogen atoms, which comprises:

1) condensing an aglycone of formula K

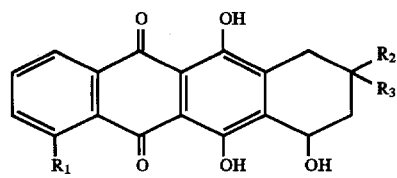

wherein $R_1$, $R_2$ and $R_3$ are as defined in claim 4, with the proviso that $R_1$, $R_2$ and $R_3$ do not represent groups bearing free primary or secondary hydroxy groups, with a sugar derivative of formula L1 or L2

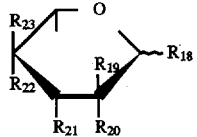

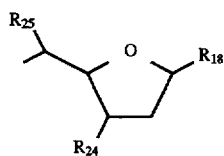

wherein $R_{18}$ represents a suitable leaving group or an activated ester residue, $R_{19}$ and $R_{20}$ are hydrogen atoms, $R_{21}$ is hydrogen, $C_1-C_4$ alkoxy or an ester residue, $R_{22}$ and $R_{23}$ are both hydrogen or one of $R_{22}$ or $R_{23}$ is hydrogen and the other is an ester residue or the group $NHCOCF_3$, $R_{24}$ is $CH_2OCOCF_3$ or has the same meaning as $R_{21}$ above defined and $R_{25}$ represents $OCOCF_3$ or $OCO(pNO_2C_6H_5)$, then (vi) deblocking the amino and hydroxy groups, and, if desired, converting the resulting said compound of formula A into a pharmaceutically acceptable salt thereof.

30. A process for producing an anthracycline of formula A as defined in claim 5 wherein $R_{13}$ is E or F, which comprises:

1) reacting an anthracycline of formula A which has a primary amino group, with an halo-acyl derivative of formula E1 or F1

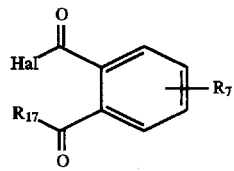

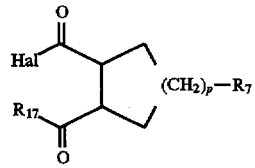

wherein $R_7$ is as defined in claim 4, Hal represents halogen atom and $R_{17}$ is an alkoxy residue, and, if desired, 2) treating the resultant mono-amino-acyl derivative with base to form groups of formula E or F, 3) if desired, converting the resulting compound into a pharmaceutically acceptable salt thereof.

31. A pharmaceutical composition which comprises as active ingredient, an anthracycline of formula A as defined in claim 5 or a pharmaceutically acceptable salt thereof in admixture with a pharmaceutically acceptable carrier or diluent.

* * * * *

UNITED STATES PATENT AND TRADEMARK OFFICE
CERTIFICATE OF CORRECTION

PATENT NO. : 5,744,454
DATED : April 28, 1998
INVENTOR(S) : Antonino SUARATO, et al.

It is certified that error appears in the above-identified patent and that said Letters Patent is hereby corrected as shown below:

On the title page, Item [30] Foreign Application Priority Number is incorrect. It should read:

--Sep. 8, 1994 [GB] United Kingdom............... 9418260.7

Signed and Sealed this

Eighth Day of September, 1998

Attest:

BRUCE LEHMAN

Attesting Officer        Commissioner of Patents and Trademarks

UNITED STATES PATENT AND TRADEMARK OFFICE
CERTIFICATE OF CORRECTION

PATENT NO. : 5,744,454
DATED : APRIL 28, 1998
INVENTOR(S) : ANTONINO SUARATO, ET AL.

It is certified that error appears in the above-identified patent and that said Letters Patent is hereby corrected as shown below:

Column 13, line 44 "fibrilis" should read --fibrils--.

Column 13, line 53 "angiopaty" should read --angiopathy--.

Column 14, line 12 "aggregate" should read --aggregates--.

Column 14, line 13 "distrofic nevrites" should read --dystrophic neurites--.

Column 14, line 19 "reteining" should read --retaining--.

Column 14, line 20 "β 142" should read --β1-42--.

Column 14, line 26 "propertiy" should read --property--.

Column 14, line 39 "fibrilogenic" should read --fibrillogenic--.

Column 14, line 40 "biifrangence" should read --birefringence--.

Column 14, line 41 "β-sheets" should read --β-sheet--.

Column 15, line 47 "seseme" should read --sesame--.

Column 15, line 50 "cetyl" should read --acetyl--.

UNITED STATES PATENT AND TRADEMARK OFFICE
CERTIFICATE OF CORRECTION

PATENT NO.   : 5,744,454
DATED        : APRIL 28, 1998
INVENTOR(S)  : ANTONINO SUARATO, ET AL.

It is certified that error appears in the above-identified patent and that said Letters Patent is hereby corrected as shown below:

Column 16,   line 21 "which have been above." should read --which have been described above.--.

Column 18,   line 52 delete "were"

Column 18,   line 54 "solution of phosphate buffer pH5, 10 mM" should read --10 mM solution of phosphate buffer pH5,--.

Column 18,   line 60 "fibrilogenesis" should read --fibrillogenesis--.

Signed and Sealed this

Ninth Day of March, 1999

Attest:

Q. TODD DICKINSON

Attesting Officer    Acting Commissioner of Patents and Trademarks